(12) United States Patent
Lee

(10) Patent No.: US 8,435,573 B2
(45) Date of Patent: May 7, 2013

(54) SECOND RUN GINSENG WINE

(75) Inventor: In Sung Lee, Toronto (CA)

(73) Assignee: In Sung Lee, Toronto, Ontario (CA)

(*) Notice: Subject to any disclaimer, the term of this patent is extended or adjusted under 35 U.S.C. 154(b) by 304 days.

(21) Appl. No.: 12/562,764

(22) Filed: Sep. 18, 2009

(65) Prior Publication Data

US 2010/0009029 A1 Jan. 14, 2010

Related U.S. Application Data

(63) Continuation-in-part of application No. 11/163,296, filed on Oct. 13, 2005, now Pat. No. 7,608,287.

(51) Int. Cl.
*A61K 36/254* (2006.01)
*A61K 36/258* (2006.01)

(52) U.S. Cl.
USPC .......................................................... 424/728

(58) Field of Classification Search ........................ None
See application file for complete search history.

(56) References Cited

FOREIGN PATENT DOCUMENTS

| CN | 101531961 A | | 9/2009 |
|---|---|---|---|
| JP | 03210172 A | * | 9/1991 |
| JP | 3210172 A | | 9/1991 |
| KR | 20040026429 A | | 3/2004 |
| KR | 100884044 B1 | | 2/2009 |
| WO | WO 2007/043017 A2 | | 4/2007 |

OTHER PUBLICATIONS

"WineWorldFDW: recipes". Internet Archive Date: Apr. 9, 2001 [Retrieved from the Internet on: Jan. 4, 2012]. Retrieved from: <URL: http://web.archive.org/web/20010405210431/http://www.wineworldfdw.com/wine_recipes.html>.*
"WineWorldFDW: wine making". Internet Archive Date: Nov. 29, 2001 [Retrieved from the Internet on: Jan. 4, 2012]. Retrieved from: <URL: http://web.archive.org/web/20011129095534/http://www.wineworldfdw.com/wine_making.html>.*
"Winemaking: Hydrometer". Internet Archive Date: Apr. 9, 2001 [Retrieved from the Internet on: Jan. 4, 2012]. Retrieved from: <URL: http://web.archive.org/web/20010409193646/http://winemaking.jackkeller.net/hydrom.asp>.*
"Winemaking: finishing your wine". Internet Archive Date: Apr. 9, 2001 [Retrieved from the Internet on: Jan. 4, 2012]. Retrieved from: <URL: http://web.archive.org/web/20010409193718/http://winemaking.jackkeller.net/finishin.asp>.*
(U1) "Making Dried Root Tinctures". Internet Archive Date: Jun. 24, 2004 [Retrieved from the Internet on: Jan. 4, 2012]. Retrieved from the Internet: <URL: http://web.archive.org/web/20040624073633/http://www.susunweed.com/herbal_ezine/May04/healingwise.htm>.*
(V1) "Fresh or Dried?". Internet Archive Date: Aug. 6, 2002 [Retrieved from the Internet on: Jan. 4, 2012]. Retrieved from the Internet: <URL:http://web.archive.org/web/20020806033712/http://apinchof.com/freshdried1001.html>.*
A.R. Harding. Ginseng and Other Medicinal Plants. A.R. Harding: Ohio, 1908. p. 156.
Herbal Supplements. Internet Archive Date: Jun. 6, 2002 [Retrieved from the Internet on Sep. 15, 2008]. Retrieved from: <http://web.archive.org/web/*/http://spineuniverse.com/displayarticle.ph p/article1064.html.> p. 1.
Retrieved from: <http://web.archive.org/web/*/http://www.quickchange.com/ginsengstore/faqs.html>. Internet Archive Date: Mar. 8, 2000 [Retrieved from the Internet: Jan. 28, 2008].
"The Winemaking Home Page Winemaking: the Basic Steps," Internet Archive Date: Feb. 3, 2001 [Retrieved from the Internet on: Jul. 24, 2007], Retrieved from: <URL: http://web.archive.org/web/*/http://winemaking.jackkeller.net/basics.asp>, pp. 1 and 2.
"The Wintemaking Home Page. Winemaking: the Basic Steps, Extracting Flavor," Internet Archive Date: Sep. 6, 2004 [Retrieved from the Internet on: Jul. 24, 2007], Retrieved from: <URL: http://web.archive.org/web/*/http://winemaking.jackkeller.net/extracting.asp>, pp. 2 and 3.
"The Winemaking Home Page, Winemaking: the Basic Steps. Additives and Other Ingredients." [Retrieved from the Internet on: Jul. 24, 2007], Retrieved from: <URL: http://web.archive.org/web/*/http://winemaking.jackkeller.net/adding.asp>, pp. 1-3.
Retrieved from: <http://web.archive.org/web/*/http://wynboer.co.za/recentarticles/0411enzyme s.php3.> Internet Archive Date: Dec. 9, 2004 [Retrieved from the Internet on: Jan. 28, 2006].

* cited by examiner

*Primary Examiner* — Amy L Clark
(74) *Attorney, Agent, or Firm* — Joseph Hyosuk Kim; JHK Law

(57) ABSTRACT

The present application discloses a process for making second run ginseng wine.

14 Claims, No Drawings

SECOND RUN GINSENG WINE

CROSS-REFERENCE TO RELATED APPLICATIONS

The present application is a continuation-in-part of U.S. application Ser. No. 11/163,296, filed Oct. 13, 2005 now U.S. Pat. 7,608,287, which is allowed, the contents of which are incorporated by reference in their entirety.

BACKGROUND OF THE INVENTION

1. Field of the Invention

The present invention relates to a process for the production of ginseng wine, in particular second run ginseng wine.

2. General Background and State of the Art

Ginseng is a human-shaped root that is one of the most popular healing herbs of the East and West used to combat weakness and give extra energy. Ginseng, prized for millennia, has an ancient history and now it is an extremely popular herb with a wide range of therapeutic uses.

The genus name *Panax* is derived from the Latin word "panacea" meaning "cure-all" (Named by German scientist C. A. Meyer in 1842).

Since the 1940s, ginseng has been one of the most highly researched herbs in the world. There are more than three thousand scientific studies performed on ginseng. Results of many high level health studies throughout the world demonstrate that ginseng possesses a large variety of therapeutic effects on the body including benefits to the central nervous system, cardiovascular system, stress (mental and emotional), fatigue, aging, and so on.

In recent years, ginseng has been promoted in the West as a tonic and a rejuvenator. Thus, there is strong evidence that ginseng has many positive effects on the body and the mind.

Ginseng species includes *Panax ginseng* (Korean ginseng), *Panax quinquefolius* (North American ginseng), *Panax japonicum* (Japanese ginseng), *Panax notoginseng* (san-qi ginseng), and *Panax pseudoginseng* (Himalayan ginseng).

Siberian ginseng (Eleutherococcus senticosus) is actually not a true ginseng species, but the properties and uses of all of these are similar and are generally referred to as ginseng.

Results of one study showed that the administration of *Panax ginseng* extract at doses of 3 g/65 Kg body weight 40 minutes after the last drink enhanced the rate of blood alcohol clearance in healthy male volunteers.

Some of the main chemical components of ginseng include at least 13 different saponins, collectively known as ginsenosides; starch; glycosides; sterols; volatile oil; polysaccharides; minerals; various flavonoids; vitamin-Bs (thiamin, riboflavin, niacin, pantothenic acid, and cobalamin); biotin; choline; pectin; phytoestrogens; and simple sugars (glucose, fructose, sucrose, maltose, and trisaccharides). It should be noted that the components may vary depending on the species and the age of the plant.

Possible therapeutic benefits of Ginseng include:

1) Stimulant: Ginseng improves mental performance, especially in older people. Ginseng contains choline, a chemical in the brain that is essential for learning and memory retention.

2) Antioxidant: Ginseng contains antioxidants, substances that prevent cellular damage due to oxidation, exposure to unstable molecules called free radicals.

3) Antiaging: Ginseng exhibited antisenility effects and led to the relief of age-related symptoms in a group of middle aged and elderly subjects.

4) Anticancer: Results of many studies found that unpurified saponins, compounds found in ginseng, inhibited the growth of cancer cells and actually converted diseased cells into normal cells. Ginseng also helps the body to cope with the side effects of chemotherapy.

5) Adaptogenic: Ginseng's remarkable 'adaptogenic' quality (helping the body to adapt to stress, fatigue, and cold) has been confirmed.

6) Menopause: Ginseng contains compounds that are similar in action to estrogen, the female sex hormone.

7) Antidiabetic: Ginseng helps the body maintain normal blood sugar and cholesterol level, and stimulates a range of immune system and endocrine responses.

The present invention should be distinguished from "wine-like ginseng liquor," which is a type of liquor. Liquor is not wine. Strictly speaking, liquor is made by distilling fermented products to obtain a spirit. "Liquor" is "unfermented or incompletely fermented, sugar-bearing liquid from which wine is made. It is also the liquid portion of a must." And "must" is the combination of basic ingredients, both solid and liquid, from which wine is made. Therefore, liquor is not wine at all.

In addition, what has commonly been seen in relation to ginseng on the market is in the form of tea, and ginseng roots soaked in a jar of liquor or spirits made of rice, grain, or fruit. However, this is not the process of wine-making from ginseng as in the subject matter of the present invention. Commonly on the market, rice or other grain wine is flavored with ginseng by adding some portion of ginseng (less than 5% of total base ingredient). Such are sometimes commercially called "ginseng wine". They abound in the marketplace. Also sold are wines or spirits in which ginseng is soaked for a certain period of time. Others include wines or spirits in which ginseng is soaked with other herbs for a certain period. Fruit wines in which ginseng extract is added are also sometimes called ginseng wine. In other words, currently in the marketplace alcohol or wine that contains an extract of ginseng is generally called "ginseng wine", and this must be distinguished from the process of preparing the ginseng wine described in the present application, which is made straight from ginseng.

In the art of wine making, there are first run wine and second run wine. The first run wine is made by fermentatively processing the original raw material. However, second run wine is made if there is enough desirable characteristics to be still extracted from the leftover processed residues after the first run. There is a need in the art to make beverages such as wine that imparts nutritional and health benefits of ginseng.

SUMMARY OF THE INVENTION

In one aspect of the invention, for background purposes, first run ginseng wine may be produced comprising the following steps:

(i) combining ground ginseng, boiling water and sugar in a sterilized primary fermentor to form a mixture;

(ii) measuring specific gravity of the mixture when the temperature of the mixture reaches room temperature, and adding purified cool water and/or sugar until the specific gravity reaches a level between 1.120 and 1.080;

(iii) adding yeast or yeast culture to the mixture and stirring the mixture to add oxygen and to release accumulated heat created during primary fermentation;

(iv) racking off lees of the wine into a sterilized secondary fermentor for anaerobic fermentation when the specific gravity reading after the primary fermentation reaches 1.020 or less, and anaerobically fermenting the wine, wherein the remaining lees are optionally pressed to release additional wine which may be combined with the free-run wine leaving behind ginseng residue to be used in making second-run wine;

(v) racking the wine at a specific gravity reading of about 0.998 to about 0.995 after the anaerobic fermentation into a sterilized container, and further anaerobically fermenting the wine; and (vi) racking the wine again into a sterilized container to achieve the clearer and clean-tasting wine.

In this process, the ground ginseng may be fresh ginseng or boiled ginseng. Preferably, the ground ginseng is fresh ginseng. Further, the ground ginseng may be boiled and simmered for about 15-30 minutes before the fermentation. In one embodiment of the invention, in step (i) above, the ginseng may be present in the mixture at about 0.05 Kg to about 0.2 Kg per liter of water, preferably at about 0.08 Kg to about 0.15 Kg per liter of water.

Optionally, the ginseng wine is fermented with the skins and pulp of ginseng. Preferably, the right combination of water, sugars, and acids should be provided based on the base ingredients for the proper fermentation to make a stable, tasty, and healthy wine. Proper temperature and fermentation period of time should also be provided for the effective fermentation.

In another embodiment of the invention, in steps (i)-(ii), the sugar may be included in the mixture at about 0.15 Kg to about 0.45 Kg per liter of water, preferably from about 0.2 Kg to about 0.4 Kg per liter of water.

In another aspect of the invention, an acidic substance may be added to the mixture in step (ii), and the acidic substance may be citric juice such as lemon juice.

Still further, tannin or sulfur dioxide may be added to the mixture in step (ii), wherein if sulfur dioxide is added, the mixture may be allowed to settle for about 24 hours.

In further other aspect of the invention, in step (ii), the maximum amount of sugar added may be about 0.4 Kg per liter of water.

Further in the process described above, in step (iii), the primary fermentation may be carried out at about 18 to about 26 degrees C., preferably for about seven to twelve days.

In yet another embodiment, in step (iv) of the process described above, the secondary fermentation may be carried out at about 15 to 23 degrees C., preferably for about two to three weeks. A fining agent may be added to the wine.

In step (iv) above, after racking of lees after primary fermentation, the ginseng residue may be further pressed to make additional wine, which may be optionally added to the free-run first run wine. The ginseng residue left over after racking or pressing in step (iv) may be used as the starting material for making second run wine. Preferably, the ginseng residue starting material for the second run wine is obtained after pressing the lees after primary fermentation and using the left over ginseng residues.

In one aspect, the invention is directed to a process for the preparation of second run ginseng wine, said process comprising:

(i) obtaining solid ginseng residue after first primary fermentation for the first run wine making process;

(ii) combining the ginseng residue from (i) with water in which sugar is dissolved, into a sterilized second primary fermentor to form a mixture;

(iii) measuring specific gravity of the mixture of (ii) when the temperature of the mixture reaches room temperature, and adding purified cool water and/or sugar until the specific gravity reaches a level between 1.080 and 1.095;

(iv) after second primary fermentation of the mixture of (iii) stirring the mixture until the specific gravity reaches between 1.005 and 1.015, racking free-run wine off lees of the second primary fermentation mixture into a sterilized secondary fermentor for the second run wine making process for anaerobic fermentation;

(v) racking the wine at a specific gravity reading of about 0.998 to about 0.995 after the anaerobic fermentation of (iv) into a sterilized container, and further anaerobically fermenting the wine; and (vi) racking the wine again into a sterilized container to produce the second run ginseng wine.

This method may preferably further comprise pressing the lees after step (iv) to release additional wine. The additional wine may be optionally combined with the free run wine of step (iv). The temperature of the water in which sugar is dissolved in step (ii) may be 32-38 degree C.

In yet another aspect of the invention, second run ginseng wine may be made with the ginseng residue left over from the primary fermentation, and may include the following steps without being limited to the recited steps:

(i) grinding fresh ginseng root to produce ground ginseng root, optionally boiling said ground ginseng root, and combining said ground ginseng root or boiled ground ginseng root with boiling water and sugar in a sterilized first primary fermentor to form a mixture;

(ii) measuring specific gravity of the mixture when the temperature of the mixture reaches room temperature, and adding purified cool water and/or sugar until the specific gravity reaches a level between 1.120 and 1.080;

(iii) adding yeast or yeast culture to the mixture and stirring the mixture to add oxygen and to release accumulated heat created during a first primary fermentation;

(iv) punching down a layer of solid ginseng content that forms on top of the mixture during the first primary fermentation and stirring the mixture to impart ingredients and flavor from the solid ginseng to the mixture;

(v) after the first primary fermentation until the specific gravity reading reaches 1.020 or less, racking free-run wine off lees of the first primary fermentation mixture into a sterilized first secondary fermentor, and optionally pressing the lees after racking to make additional wine, leaving behind ginseng residue to be used in making second run ginseng wine;

(vi) combining the ginseng residue from the left over residue after the racking and/or pressing step in (v) with water in which sugar is dissolved, in a sterilized second primary fermentor to form a mixture for the second run ginseng wine;

(vii) measuring specific gravity of the mixture of (vi) when the temperature of the mixture reaches room temperature, and adding purified cool water and/or sugar until the specific gravity reaches a level between 1.080 and 1.095;

(viii) after second primary fermentation of the mixture of (vii) stirring the mixture until the specific gravity reaches between 1.005 and 1.015, racking free-run wine off lees of the second primary fermentation mixture into a sterilized second secondary fermentor;

(ix) optionally pressing said lees of (viii) to release additional wine which is optionally combined with the free-run wine of (viii) and anaerobically fermenting the wine in the second secondary fermentor;

(x) racking the wine at a specific gravity reading of about 0.998 to about 0.995 after the anaerobic fermentation of (ix) into a sterilized container, and further anaerobically fermenting the wine; and (xi) racking the wine again into a sterilized container to produce the second run ginseng wine.

In the above process, the ground ginseng root may be boiled or if fresh ginseng root, rinsed before said grinding. The ground ginseng root may be boiled and simmered for about 15-30 minutes before the fermentation. In (i), the ground ginseng root may be present in the mixture in an amount of about 0.05 to about 0.2 kilogram of ginseng root per liter of water. The ground ginseng root may be present in the mixture in an amount of about 0.08 to about 0.15 kilogram of ginseng root per liter of water. In (i) and (ii), the sugar may be included in the mixture in an amount of about 0.15 to about 0.45 kilogram of sugar per liter of water, and the sugar may be included in the mixture in an amount of about 0.2 to about 0.4 kilogram of sugar per liter of water. In (ii), the maximum amount of sugar added may be in an amount of about 0.4 kilogram of sugar per liter of water. In (iii), the primary fermentation may be carried out at about 18 to about 26 degrees C. for about seven to twelve days.

In (vi), where the starting material is the ginseng residue for the preparation of the second run wine, the temperature of the water in which sugar is dissolved, which is added to the ginseng residue may be about 32-38 degree C. In step (vi) acid or tannin may be added to the mixture. Optionally, in step (vi) no yeast may be added to the mixture. In step (vi), the second primary fermentation may be carried out for about nine to twelve days.

The invention is also directed to a process for the preparation of second run ginseng wine with an alcohol content of 10 to 12%, said process comprising:

(i) grinding fresh ginseng root to produce ground ginseng root, optionally boiling said ground ginseng root, and combining said ground ginseng root or boiled ground ginseng root with boiling water and sugar in a sterilized first primary fermentor to form a mixture;

(ii) measuring specific gravity of the mixture when the temperature of the mixture reaches room temperature, and adding purified cool water and/or sugar until the specific gravity reaches a level between 1.120 and 1.080;

(iii) adding yeast or yeast culture to the mixture and stirring the mixture to add oxygen and to release accumulated heat created during a first primary fermentation;

(iv) punching down a layer of solid ginseng content that forms on top of the mixture during the first primary fermentation and stirring the mixture to impart ingredients and flavor from the solid ginseng to the mixture;

(v) after the first primary fermentation (of the first-run wine) until the specific gravity reading reaches 1.020 or less, racking free-run wine off lees of the first primary fermentation mixture and optionally further pressing the lees after racking to make additional wine, into a sterilized first secondary fermentor, leaving behind ginseng residue to be used in making second run ginseng wine;

(vi) combining the ginseng residue from (v) obtained by the racking and/or pressing step with water in which sugar is dissolved, in a sterilized second primary fermentor to form a mixture;

(vii) measuring specific gravity of the mixture of (vi) when the temperature of the mixture reaches room temperature, and adding purified cool water and/or sugar until the specific gravity reaches a level between 1.080 and 1.095;

(viii) after second primary fermentation of the mixture of (vii) stirring the mixture until the specific gravity reaches between 1.005 and 1.015, racking free-run wine off lees of the second primary fermentation mixture into a sterilized second secondary fermentor;

(ix) optionally pressing said lees of (viii) to release additional wine which is optionally combined with the free-run wine of (viii) and anaerobically fermenting the wine in the second secondary fermentor;

(x) racking the wine at a specific gravity reading of about 0.998 to about 0.995 after the anaerobic fermentation of (ix) into a sterilized container, and further anaerobically fermenting the wine; and (xi) racking the wine again into a sterilized container when the fermentation process is completely over to produce the second run ginseng wine.

In (vi), the temperature of the water in which sugar is dissolved, which is added to the ginseng residues may be 32-38 degree C. Acid or tannin may be added to the mixture. And optionally, no yeast may be added to the mixture. Moreover, the second primary fermentation may be carried out for about nine to twelve days.

In a further embodiment, the invention is directed to the first run or second run or mixture thereof of the wine produced by the above described process.

DETAILED DESCRIPTION OF THE INVENTION

In the present application, "a" and "an" are used to refer to both single and a plurality of objects.

As used herein, "fining agent" refers to adsorptive or reactive substance to reduce or remove the concentration of one or more undesirable components in the wine. Fining agents are used to achieve clarity and to improve color, flavor and physical stability. Fining agents can be grouped according to their chemical nature and mode of action, such as 1. Earths: bentonite; 2. Proteins: gelatin, isinglass, casein, albumen; 3. Polysaccharides: agars; 4. Carbons; 5. Synthetic polymers: PVPP; 6. Silicon dioxide (kieselsol); and 7. Others, including chelators and enzymes.

As used herein, "free-run wine" refers to the ginseng wine before undergoing pressing.

As used herein, "fresh" ginseng refers to ginseng that has not been boiled, and may include whole or diced peeled or unpeeled ginseng root.

As used herein, "lees" refers to solids that result from fermentation, that are found on the bottom of the container.

As used herein, "stabilizing agent" refers to an agent that is added to the wine to eliminate the risk of microbial spoilage, to reduce the effects of oxidation, to ensure fermentation does not re-occur in sweet wine, and to maintain color stability and clarity throughout the aging process.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

First-Run Ginseng Wine

Ingredients For First-Run Ginseng Wine (For About 6 U.S. Gallons/23 Liters Of Wine)

Fresh ginseng roots: 2-3 Kg
Water (purified): 20-24 liters
Sugar: 5.0-8.0 Kg
Wine yeasts: 5-10 g
Acids (tartaric, citric, or acid blends (with tartaric/malic/citric acids): 3.0-3.9 pH
Sulfur dioxide (optional): 30-50 ppm
Tannin (optional): 8-12 g Fining agents (optional): Pectic enzyme, bentonite, amylase or diastase, isinglass, and/or tannins (use according to the directions provided by the maker).

Stabilizers: Potassium sorbate (125-200 ppm) or wine conditioner (up to 250 ml)

First-Run Ginseng Winemaking Process

The process of making ginseng wine is described below, however, it is understood that a variation in the order of the steps is contemplated within the scope of the invention so long as ginseng wine is made. Further, the process exemplified here is directed to making about 23 liters or 6 gallons of wine, which can be scaled up or down as desired.

The fresh ginseng roots are rinsed thoroughly to remove soil, harmful bacteria, insects, and any chemical residues. Any moldy and brown spots should be cut out. The washed ginseng roots are ground after adding 3-4.5 liters of cold water. The ground ginseng roots can be optionally boiled before the fermentation. If boiled, the ground ginseng is brought to a boil in 6-9 liters of water and then simmered for about 15-30 minutes over medium heat.

The ground ginseng roots are then placed in a sterilized primary fermentor (vessel for aerobic fermentation which is the initial and rapid fermentation) and combined with boiling water (3-5 liters) in which sugar is dissolved. In particular, the sugar to be used may be a fermentable sugar such as dextrose (corn sugar) or sucrose (beet or cane sugar).

When the mixture has cooled down to room temperature, the specific gravity reading should be taken. Purified cool water and/or sugar is added until the specific gravity reading of the mixture reaches a level between 1.080 and 1.120 to get about 11 to 17 percent alcohol rate.

Acids are added to the mixture, and tannins and sulfur dioxide can also be added if desired. If sulfur dioxide is added, the sulfited mixture is allowed to settle for about twenty-four (24) hours.

Wine yeasts (or yeast culture) are added to the mixture and the fermentor should be covered to protect the mixture from any insect and dust. The mixture is allowed to stand at around 18-26 degrees C. (65-80 degrees F.).

During the primary fermentation, the cap (the layer of solid ginseng contents that forms on top of the mixture) should be punched down and the mixture stirred several times a day to 1) mix the ginseng contents with the mixture to impart ingredients and flavor; 2) introduce a limited amount of oxygen required by the growing population of yeasts during the vigorous initial fermentation; and 3) release the accumulated heat created by the fermentation.

When the fermentation has subsided after seven to twelve days of vigorous primary fermentation (at specific gravity reading of 1.020 or less), the wine is racked off the lees into the sterilized secondary fermentor (vessel for anaerobic fermentation which is slower fermentation). The remaining lees are optionally pressed to release additional wine which is richer in desirable extracts and ginseng flavors than the free-run, and leaving behind ginseng residue. This pressed wine is added to the free-run wine. However, the residual ginseng is used as the starting material for making the second-run wine.

The secondary fermentor should be filled leaving enough room between the surface of the wine and the bottom of the fermentation lock to prevent the wine from overflowing. Ginseng forms many bubbles because of its components, including saponins known as ginsenosides.

The airlock (fermentation lock) should be installed on the fermentor to protect the wine from contact with air while still allowing the carbon dioxide gas to escape. The airlock may be filled with water or sulfite solution to approximately half full in each chamber.

The wine is allowed to stand at around 15-23 degrees C. (60-75 degrees F.) for two to three weeks for the secondary fermentation until the specific gravity has fallen to 0.998-0.995, at which time the wine is racked again into another sterilized container, leaving behind as much lees as possible. The new container should be filled as fully as possible. If the container is not filled, it may be preferably filled with purified cool water, or sugar water, or same kind of wine. And the container should be closed with an airlock. During this stage, sluggish fermentation may occur.

When the fermentation process is completely over, there is no more activity inside the air-lock. The specific gravity reading should be taken to check the alcohol levels. The wine can be racked again into another sterilized container to achieve the clearer and clean-tasting wine.

Correctly made ginseng wine should not normally require a clarification process. But, if the wine remains cloudy after two to three months after fermentation has ceased, there is a possibility that it will not clear naturally. In this case, a clarification process should be performed with proper fining agents. Filtration is another option for clarification and stabilization as well.

The wine should be stabilized even after successful fermentation to prevent the possibility of refermentation after bottling. There are several stabilization methods, such as adding stabilizing agent, filtration, pasteurization, cold stabilization, and centrifuging (for the large volume of wine).

The wine is allowed to stand for several months in a cool and dark place for bulk aging. After several months of bulk aging, 30 ppm of sulfur dioxide is added if desired, and the wine is then bottled and aged in a cool and dark place. If the wine has not already gone through the filtration process, the wine can be filtered before the bottling. At this point, the wine could have about 11-17% alcohol by volume. The wine will be quite drinkable soon after bottling but will improve with bottle aging in a cool place for a while.

Ginseng wine may be served at room temperature, chilled, or warm (but never boiled) as a versatile drink before, during and after meals. The amount of ethanol alcohol actually formed depends on the several factors including the amount of sugar, nutrient level of the materials (ginseng in this case), yeast species, and the general condition of fermentation. If the mixture is too rich with sugar, it may actually retard fermentation and clarification.

Second-Run Ginseng Wine

Second-run ginseng wine is made from the leftover ginseng residue after pressing the mixture at the end of the primary fermentation of the first-run ginseng wine.

1) In a sterilized primary fermentor, the ginseng residue is combined with water in which sugar is dissolved. The sugar is dissolved in the boiling water and cooled down to between 32 and 38 degree C. to be combined with the ginseng residue to make a mixture.

2) It is understood that no yeast or yeast nutrients are required if the ginseng residue is combined with the water above of which temperature is between 32 and 38 degree C.

3) The specific gravity of the mixture may be between 1.080 and 1.095.

Ingredients for Second-Run Ginseng Wine (For about 6 U.S. gallon/23 Liters Of Wine)

Ginseng residue: 6.5 Kg
Water (purified): 22-23 liters
Sugar: 5.5-7.0 Kg
Acid: 3.0-3.5 pH
Sulphur dioxide: 30-50 ppm
Tannin(optional): 10-12 g
Pectic enzyme(optional): 5-6 g Second-Run Ginseng Winemaking Process 1) The ginseng residue is placed in a sterilized primary fermentor.

2) Sugar is dissolved in the boiling water and cooled down to 32-38 degree C.

3) The water in which sugar is dissolved is poured over the ginseng residue. Specific gravity of the mixture should reach a level between 1.080 and 1.095.

4) Acids are added to the mixture and tannins are also added if desired.

5) No yeast is added to the mixture.

6) During the primary fermentation, the mixture is stirred several times a day to mix the residual ginseng content with the mixture to impart ingredients and flavour.

7) After 9 to 12 days when the specific gravity reaches between 1.005 and 1.015, the wine is racked off the lees into a sterilized secondary fermentor. The remaining lees are pressed to release additional wine. The pressed wine is added to the free-run wine.

8) The process for forming the second-run wine is otherwise similar to the first-run ginseng wine. The alcohol content of the second-run wine may be about 10-12% alcohol by volume.

* * *

Those skilled in the art will recognize, or be able to ascertain using no more than routine experimentation, many equivalents to the specific embodiments of the invention specifically described herein. Such equivalents are intended to be encompassed in the scope of the claims.

What is claimed:

1. A method of making a second run ginseng wine, said method comprising:
   (i) grinding fresh ginseng root to produce ground ginseng root, optionally boiling said ground ginseng root to provide boiled ground ginseng root, and combining said ground ginseng root or boiled ground ginseng root with boiling water and sugar in a sterilized first primary fermenter to form a first mixture;
   (ii) measuring specific gravity of the first mixture when the temperature of the first mixture reaches room temperature, and adding purified cool water and/or sugar until the specific gravity reaches a level between 1.120 and 1.080 to provide a second mixture;
   (iii) adding yeast or yeast culture to the second mixture to provide a first primary fermentation, wherein a first primary fermentation mixture is obtained, stirring the first primary fermentation mixture to add oxygen and to release accumulated heat created during the first primary fermentation, and wherein a layer of solid ginseng content is obtained on top of the first primary fermentation mixture;
   (iv) punching down the layer of solid ginseng content and stirring first primary fermentation mixture to impart ingredients and flavor from the solid ginseng content to the mixture and obtaining a free-run ginseng wine and lees;
   (v) racking the free-run ginseng wine off lees of the first primary fermentation mixture into a sterilized first secondary fermenter to provide ginseng residue, and optionally further pressing said lees to release additional ginseng wine;
   (vi) combining the ginseng residue with water, wherein the water contains dissolved sugar, in a sterilized second primary fermenter to form a mixture;
   (vii) measuring specific gravity of the mixture of (vi) when the temperature of the mixture of (vi) reaches room temperature, and adding purified cool water and/or sugar until the specific gravity reaches a level between 1.080 and 1.095 to provide a second primary fermentation mixture;
   (viii) stirring the second primary fermentation mixture until the specific gravity reaches a level between 1.005 and 1.015, obtaining a second free-run ginseng wine and lees of the second primary fermentation mixture, racking the second free-run ginseng wine off lees of the second primary fermentation mixture into a sterilized second secondary fermenter, wherein the second free-run wine is subjected to anaerobic fermentation to provide ginseng wine;
   (ix) racking the ginseng wine of (viii) at a specific gravity of about 0.995 to about 0.998 after anaerobic fermentation into a sterilized container; and
   (x) further anaerobically fermenting the wine of (ix) and racking the resulting wine into a sterilized container to provide the second run ginseng wine.

2. The method according to claim 1, further comprising pressing the lees after step (viii) to release additional wine.

3. The method according to claim 2, wherein the additional wine is combined with the free run wine of step (viii).

4. The method according to claim 1, wherein in (vi), wherein the temperature of the water in which sugar is dissolved is 32-38 degree C.

5. The method according to claim 1, wherein in step (vi) acid or tannin is added to the mixture.

6. The method according to claim 1, wherein in step (vi) no yeast is added to the mixture.

7. The process method according to claim 1, wherein in (vi), the second primary fermentation is carried out for about nine to twelve days.

8. The method according to claim 1, wherein in step (vi) no yeast is added to the mixture.

9. The method according to claim 1, wherein in (vi), the second primary fermentation is carried out for about nine to twelve days.

10. A method of making a second run ginseng wine with an alcohol content of 10 to 12%, said method comprising:
   (i) grinding fresh ginseng root to produce ground ginseng root, optionally boiling said ground ginseng root to provide boiled ground ginseng root, and combining said ground ginseng root or boiled ground ginseng root with boiling water and sugar in a sterilized first primary fermenter to form a first mixture;
   (ii) measuring specific gravity of the first mixture when the temperature of the first mixture reaches room temperature, and adding purified cool water and/or sugar until the specific gravity reaches a level between 1.120 and 1.080 to provide a second mixture;
   (iii) adding yeast or yeast culture to the second mixture to provide a first primary fermentation, wherein a first primary fermentation mixture is obtained, stirring the first primary fermentation mixture to add oxygen and to release accumulated heat created during the first primary fermentation, and wherein a layer of solid ginseng content is obtained on top of the first primary fermentation mixture;
   (iv) punching down the layer of solid ginseng content and stirring first primary fermentation mixture to impart ingredients and flavor from the solid ginseng content to the mixture and obtaining a free-run ginseng wine and lees;

(v) racking the free-run ginseng wine off lees of the first primary fermentation mixture into a sterilized first secondary fermenter to provide ginseng residue, and optionally further pressing said lees to release additional ginseng wine;

(vi) combining the ginseng residue with water, wherein the water contains dissolved sugar, in a sterilized second primary fermenter to form a mixture;

(vii) measuring specific gravity of the mixture of (vi) when the temperature of the mixture of (vi) reaches room temperature, and adding purified cool water and/or sugar until the specific gravity reaches a level between 1.080 and 1.095 to provide a second primary fermentation mixture;

(viii) stirring the second primary fermentation mixture until the specific gravity reaches a level between 1.005 and 1.015, obtaining a second free-run ginseng wine and lees of the second primary fermentation mixture, racking the second free-run ginseng wine off lees of the second primary fermentation mixture into a sterilized second secondary fermenter, wherein the second free-run wine is subjected to anaerobic fermentation to provide ginseng wine;

(ix) racking the ginseng wine of (viii) at a specific gravity of about 0.995 to about 0.998 after anaerobic fermentation into a sterilized container; and (x) further anaerobically fermenting the wine of (ix) and racking the resulting wine into a sterilized container to provide the second run ginseng wine.

11. The method according to claim 10, further comprising pressing the lees after step (viii) to release additional wine.

12. The method according to claim 10, wherein the additional wine is combined with the free run wine of step (viii).

13. The process according to claim 10, wherein in (vi), wherein the temperature of the water in which sugar is dissolved is 32-38 degree C.

14. The process according to claim 10, wherein in step (vi) acid or tannin is added to the mixture.

* * * * *